United States Patent [19] [11] Patent Number: 6,001,819
Simon et al. [45] Date of Patent: Dec. 14, 1999

[54] BACTERIAL INHIBITION WITH AN OLIGOSACCHARIDE COMPOUND

[75] Inventors: Paul M. Simon, Wilmington, Del.; David Zopf, Strafford, Pa.; Roger A. Barthelson, Kintnersville, Pa.; Karl F. Johnson, Willow Grove, Pa.

[73] Assignee: Neose Technologies, Inc., Horsham, Pa.

[21] Appl. No.: 09/054,890

[22] Filed: Apr. 3, 1998

Related U.S. Application Data

[63] Continuation of application No. 08/488,053, Jun. 7, 1995, Pat. No. 5,736,533.

[51] Int. Cl.$^6$ .................................................. A01N 43/04
[52] U.S. Cl. ................................ 514/54; 514/53; 514/61; 514/23; 514/25; 536/4.1; 536/123; 536/123.1; 536/123.13
[58] Field of Search ................................. 514/53, 54, 61, 514/23, 25; 536/4.1, 123, 123.1, 123.13

[56] References Cited

U.S. PATENT DOCUMENTS

| | | | |
|---|---|---|---|
| 4,704,360 | 11/1987 | Shoham et al. | 435/99 |
| 5,089,479 | 2/1992 | Krivan et al. | 514/25 |
| 5,217,715 | 6/1993 | Krivan et al. | 424/92 |
| 5,225,330 | 7/1993 | Ginsburg et al. | 435/7.32 |
| 5,386,027 | 1/1995 | Krivan et al. | 536/123.1 |
| 5,389,521 | 2/1995 | Krivan et al. | 435/7.33 |
| 5,399,567 | 3/1995 | Platt et al. | 514/315 |
| 5,484,773 | 1/1996 | Heerze et al. | 514/23 |
| 5,514,660 | 5/1996 | Zopf et al. | 514/25 |
| 5,620,964 | 4/1997 | Roth et al. | 514/53 |
| 5,627,163 | 5/1997 | Heerze et al. | 514/61 |
| 5,637,576 | 6/1997 | Heerze et al. | 514/61 |
| 5,661,131 | 8/1997 | Heerze et al. | 514/25 |
| 5,736,533 | 4/1998 | Simon et al. | 514/61 |
| 5,753,630 | 5/1998 | Zopf et al. | 514/25 |

FOREIGN PATENT DOCUMENTS

| | | |
|---|---|---|
| A1-0-126-043 | 11/1984 | European Pat. Off. . |
| WO 95/23605 | 9/1995 | WIPO . |

OTHER PUBLICATIONS

Paulsen et al. *Carbohydrate Research*, 137: 39–62, (1985).
Gronberg et al. *Carbohydrate Research*, 191: 261–278, (1989).
Feizi et al. *Carbohydrate Research*, 228: 289–297, (1992).
Glycotech Technical Catalog (Techniques in Glycobiology—vol. 1), pp. 33–44, (1996).

(List continued on next page.)

*Primary Examiner*—Howard C. Lee
*Attorney, Agent, or Firm*—Pennie & Edmonds LLP

[57] ABSTRACT

The present invention is directed to compositions for the treatment of respiratory infections caused by a bacteria selected from the group consisting of *S. pneumoniae*, *H. influenzae*, *H. parainfluenza*, *Burkholderia* (*Pseudomonas*) *cepacia*, and a mixture thereof, comprising a binding inhibiting effective amount of the compound of Formula I,

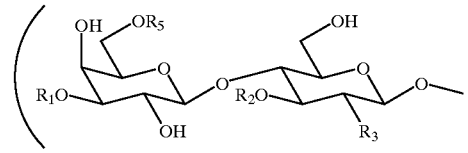

(I)

where
  $R_1$ is H, ($\beta$-1)GalNAc-, $SO_3B$ (where B is H or a cation) or a sialic acid of Formula II;

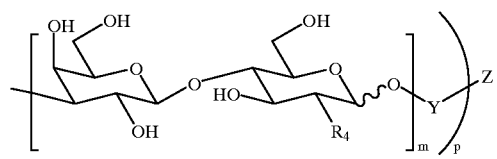

(II)

where
  $R_6$, $R_7$, $R_8$, and $R_{10}$ are each independently H, $C_{1-6}$ acyl, lactyl, $C_{1-6}$ alkyl, sulfate, phosphate, anhydro, a sialic acid of Formula II, ($\alpha$-1)Fuc, ($\beta$-1)Glc or ($\beta$-1)Gal;
  $R_9$ is NH—$C_{1-6}$ acyl, glycolylamido, amino or hydroxyl; and
  A is H or a cation;
  $R_2$ is H or ($\alpha$-1)Fuc-;
  $R_3$ and $R_4$ are each independently OH or NHAc;
  $R_5$ is H, $SO_3B$ (where B is H or a cation), or a sialic acid of Formula II as defined above;

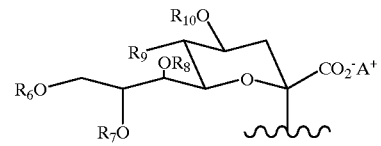

(II)

Y is a chemical bond or a linking group;
Z is H or a multivalent support;
m is 0 or 1; and
p is an integer of 1 to 1,000; with the proviso that the compound is not Gal$\beta$1-4-GlcNAc$\beta$1-3-Gal$\beta$1-4-Glc.

3 Claims, No Drawings

OTHER PUBLICATIONS

Oxford Glycosystems Catalog (Tools for Glycobiology) pp. 77–81, (1994).

Ajisaka et al., 1994, "Regioselective Transglycosylation in the Synthesis of Oligosaccharides: Comparison of β–Galactosidases and Sialidases of Various Origins", Carbohydrate Res. 259:103–115.

Kitagawa et al., 1994, "Cloning of a Novel α–2,3–Sialyltransferase that Sialylates Glycoprotein and Glycolipid Carbohydrate Groups", J. Biol. Chem. 269:1394–1401.

Llukkonen et al., 1992, "Identification of N–acetylneuraminyl α2–3 Poly–N–acetyllactosamine Glycans as the Receptors of Sialic Acid–binding *Streptococcus suis* Strains", J. Biol. Chem. 267:21105–21111.

Ramphal et al., 1991, "*Pseudomonas aeruginosa* Recognizes Carbohydate Chains Containing Type 1 (Gal–β1–3GlcNAc) or Type 2(Gal–β1–4GlcNAc) Disaccharide Units", Infection and Immunity 59:700–704.

Andersson et al., 1986, "Inhibition of Attachment of *Streptococcus pneumoniae* and *Haemophilus influenzae* by Human Milk and Receptor Oligosacchrides", J. Infectious Diseases 153:232–237.

The Journal of Infectious Disease, vol. 153, No. 2, Feb. 1986, pp. 232–237 Inhibition of Attachment of *Streptococcus pneumoniae* and *Haemophilus influenzae* by Human Milk and Receptor Oligosaccharides, Bengt Andersson, Oscar Porras, Lars Å. Hanson, Teresa Lagergård, and Catharina Svanborg–Edén.

The Journal of Infectious Diseases, vol. 151, No. 5, May 1985, pp. 859–868 The Induction of Meningeal Inflammation by Components of the Pneumococcal Cell Wall, Elaine Tuomanen, Hans Liu, Bruno Hengstler, Oto Zak, and Alexander Tomasz.

Infection and Immunity, May, 1993, pp. 1687–1693, vol. 61, No. 5, *Shigella flexneri* Transformants Expressing Type 1 (Mannose–Specific) Fimbriae Bind to, Activate, and Are Killed by Phagocytic Cells, Awni Gbarah, David Mirelman, Philippe J. Sansonetti, Renaud Verdon, Wolfgang Bernhard, and Nathan Sharon.

Infection and Immunity, Apr. 1993, pp. 1538–1543, vol. 61, No. 4, The Cell Wall Mediates Pneumococcal Attachment to and Cytopathology in Human Endothelial Cells, Sibyl Geelen, Chandrabali Bhattacharyya, and Elaine Tuomanen.

Infection and Immunity, Apr. 1981, pp. 311–317, vol. 32, No. 1, Adhesion of *Streptococcus pneumoniae* to Human Pharyngeal Epithelial Cells In Vitro: Differences in Adhesive Capacity Among Strains Isolated from Subjects with Otitis Media, Septicemia, or Meningitis or from Healthy Carriers, B. Andersson, B. Eriksson, E. Falsen, A. Fogh, L.Å Hanson, O. Nylén, H. Peterson, and C. Svanborg Eden.

Proc. Natl. Acad. Sci. USA, vol. 85, pp. 6157–6161, Aug. 1988 Microbiology, Many pulmonary pathogenic bacteria bird specifically to the carbohydrate sequence GalNAcB1–4Gal found in some glycolipids, Howard C. Krivan, David D. Roberts, and Victor Ginsburg.

*Annu. Rev. Biochem,* 1989, 58:309–50 Animal Glycosphingolipids as Membrane Attachment Sites for Bacteria, Karl–Anders Karlsson.

Molecular Microbiology(1994) 11(4) 705–713 The binding of *Pseudomonas aeruginosa* pili to glycosphingolipids is a tip–associated event involving the C–terminal region of the structural pilin subunit, K.K. Lee, H.B. Sheth, W.Y. Won, R. Sherburne, W. Paranchych, R.S. Hodges, C.A. Lingwood, H. Krivan and R.T. Irvin.

J. Exp. Med The Rockefeller University Press, vol. 168, Jul. 1988, pp. 267–277, Receptor Analogs and Monoclonal Antibodies That Inhibit Adherence of *Bordetella pertussis* to Human Ciliated Respiratory Epithelial Cells by Elaine Tuomanen, Harry Towbin, Gunter Rosenfelder, Dietmar Braun, Goran Larson, Gunnar C. Hansson, and Ross Hill.

J.Exp. Med The Rockefeller University Press, vol. 158, Aug. 1983, pp. 559–570, Identification of an Active Disaccharide Unit of a Glycoconjugate Receptor for Pneumococci Attaching to Human Pharyngeal Epithelial Cells, by Bengt Andersson, Jan Dahmen, Torbjörn Frejd, Hakon Leffler, Goran Magnusson, Ghazi Noori, and Catharina Svanborg Eden.

Am Rev Respir Dis 1986; 134:1040–1044, Adherence of Type I *Streptococcus pneumoniae* to Trachcal Epithelium of Mice Infected with Influenza A/PR8 Virus, Maris–Cristina Plotkowski, Edith Puchelle, Genevieve Beck, Jacky Jacquot, and Claude Hannoun.

*J. Clin. Invest. The American Society for Clinical Investigation, Inc.,* vol. 63 Mar. 1979 378–387, Pulmonary Alveolar Type II Cells Isolated from Rats, Release of Phosphatidylcholine in Response to β–Adrenergic Stimulation, Leland G. Dobbs and Robert J. Mason, Cardiovascular Research Institute, University of California Medical Center, San Francisco, California 94143.

*Seminars in Hematology,* vol. 18, No. 1 (Jan.), 1981, pp. 39–62, Blood Group ABH and Ii Antigens of Human Erythrocytes: Chemistry, Polymorphism, and Their Developmental Change, Sen–itiroh Hakomori.

U.S. application No. 08/488,053, filed Jun. 7, 1995, pending.

U.S. application No. 08/461,000, filed Jun. 5, 1995, pending.

U.S. application No. 08/474,199, filed Jun. 7, 1995, pending.

BACTERIAL INHIBITION WITH AN OLIGOSACCHARIDE COMPOUND

This is a continuation of application Ser. No. 08/488,053, filed Jun. 7, 1995, now U.S. Pat. No. 5,736,533.

BACKGROUND OF THE INVENTION

1. Field of the Invention

The present invention is directed to a method of treating bacterial infections caused by a bacteria selected from the group consisting of Streptococcus pneumoniae, Haemophilus influenza, Hemophilus parainfluenza, Burkholderia (Pseudomonas) cepacia and a mixture thereof using an oligosaccharide, as well as a pharmaceutical composition containing same.

2. Discussion of the Background

S. pneumoniae, H. influenza, H. parainfluenza, and Burkholderia (Pseudomonas) cepacia are pathogenic bacteria associated with respiratory diseases such as pneumonia, bacterial bronchitis, conjunctivitis, sinusitis and otitis media. In each of these conditions, the bacteria colonizes the healthy tissue of the nasopharynx, conjunctiva, lung, bronchi or ear canal, establishing a large enough population to cause the disease. The bacteria adhere to the cell-surfaces, at specific receptor sites for the bacteria.

Conventional therapy has relied on administration of antibiotics, in order to alleviate the bacterial colonization. However, antibiotic therapy is subject to the development of antibiotic resistant strains, (and can ultimately generate "super bacteria") which would not be treatable with known antibiotics. A report issued by the American Society of Microbiology, in May of 1995, indicated that more and more infectious organisms are becoming untreatable with antibiotics and that steps must be taken to reverse this trend before a public health crisis occurs.

Researchers have studied the interactions of pathogenic bacteria with tissue receptors, responsible for adherence, and have identified specific carbohydrate sequences which can inhibit bacterial adherence.

Krivan et al U.S. Pat. No. 5,386,027, report binding inhibition of specific "opportunistic pathogenic bacteria", which are associated with respiratory tract infections, with compounds containing either an internal or terminal GalNAcβ1-4-Galβ1-4-Glc sequence. The specific pulmonary pathogenic bacteria for which binding inhibition are reported are Pseudomonas aeruginosa, Haemophilus influenza, Staphylococcus aureus, Streptococcus pneumoniae, Klebsiella pneumoniae and Escherichia coli. The reference postulates that ganglioside GM1 is present in substantial amounts in human lung tissue and that pulmonary pathogenic bacteria require at least a terminal or internal GalNAcβ1-4-Gal, which is unsubstituted with sialyl residues.

Andersson et al J. Exp. Med. (1983), v. 158, p. 559–570, report binding inhibition studies on Streptococcus pneumoniae, and identify a disaccharide GlcNAc β1-3-Galβ as a specific glycoconjugate receptor. The reference reports that compound 3, NeuAcα2-3Galβ1-4-GlcNAcβ1-3-Galβ1-4-Glc-Cer had no effect at binding inhibition (page 564, first sentence under Table IV).

Rosenstein et al, Infection and Immunity (1992), vol. 60, no. 12, 5078–5084, report binding specificities for Pseudomonas aeruginosa M35 and Escherichia coli C600, isolated from cystic fibrosis patients for various oligosaccharide structures. Galβ1-4-GlcNAcβ-3-Galβ1-4-Glc was reported to have high binding activity while NeuAcα2-6-Galβ1-4-GlcNAcβ1-3-Galβ1-4-Glc showed no activity.

Ramphal et al, Infection and Immunity (1991) vol. 59, no. 2, p. 700–704, report binding inhibition studies on Pseudomonas aeruginosa to Type 1 (Galβ1-3-GlcNAc) and Type 2 (Galβ1-4GlcNAc) disaccharides. NeuAcα2-6-Galβ1-4-GlcNAcβ1-3-Galβ1-4-Glc is reported to have no activity in the direct adhesion assay.

Ginsburg et al U.S. Pat. No. 5,225,330 report a diagnostic device for absorbing microorganisms, using specific carbohydrate receptor sequences. The reference reports no activity for sialylparagoboside in binding inhibition of Mycoplasma pneumoniae (Table I, col. 11) but reports Escherichia coli inhibition of N-glycolylsialoparagloboside.

Feizi et al Biochemistry, 1994, 33, 6342–6349, report that NeuAcα2-6-Galβ1-4-GlcNAcβ1-3-Galβ1-4-Glc is not bound or is only negligibly bound by immunoglobulin E-binding protein, while NeuAcα2-3-Galβ1-3-GlcNAcβ1-3-Galβ1-4-Glc is strongly bound by this protein.

Magnani et al WO92/18610 report the use of sialyl-Le$^a$ (Neu5Acα2-3-Galβ1-3[Fucα1-4]GlcNAc) and sialyl-Le$^x$ (Neu5Acα2-3-Galβ1-4[Fucα1-3]GlcNAc) in inhibiting binding of malignant cells to endothelial cells both in vivo and in vitro.

Andersson et al J. of Infectious Diseases (1986), vol. 153, no. 2, 232–237, report that fractions of human milk inhibited the attachment of Streptococcus pneumoniae and Haemophilus influenaze to human pharyngeal or buccal epithelial cells.

Accordingly, new methods of treating bacterial infections of a bacteria selected from the group consisting of Streptococcus pneumoniae, Haemophilus influenza, Hemophilus parainfluenza, Burkholderia (Pseudomonas) cepacia and a mixture thereof, are being sought, which have a lower probability of generating antibiotic resistant strains. Anti-adhesion compounds are potentially useful candidates in this search.

SUMMARY OF THE INVENTION

Accordingly, one object of this invention is to provide a novel method of inhibiting colonization of a bacteria selected from the group consisting of S. pneumoniae, H. influenza, H. parainfluenzae, Burkholderia (Pseudomonas) cepacia and a mixture thereof, by administering a binding inhibiting effective amount of the compound of Formula I,

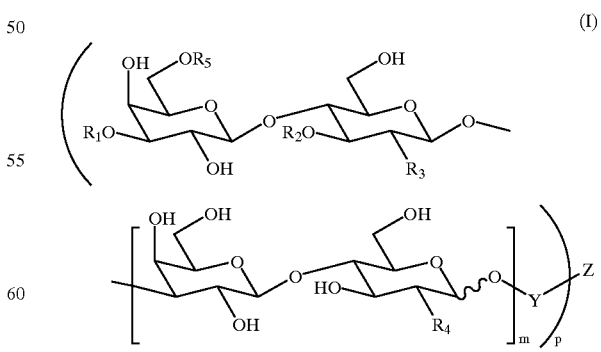

(I)

where
  $R_1$ is H, (β-1)GalNAc-, $SO_3B$ (where B is H or a cation) or a sialic acid of Formula II;

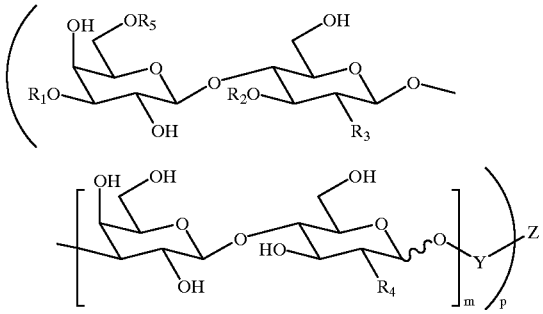

where

R$_6$, R$_7$, R$_8$, and R$_{10}$ are each independently H, C$_{1-6}$ acyl, lactyl, C$_{1-6}$ alkyl, sulfate, phosphate, anhydro, a sialic acid of Formula II, (α-1)Fuc, (β-1)Glc or (β-1)Gal;

R$_9$ is NH—C$_{1-6}$ acyl, glycolylamido, amino or hydroxyl; and

A is H or a cation;

R$_2$ is H or (α-1)Fuc-;

R$_3$ and R$_4$ are each independently OH or NHAc;

R$_5$ is H, SO$_3$B (where B is H or a cation) or a sialic acid of Formula II as defined above; and Y is a chemical bond or a linking group;

Z is H or a multivalent support;

m is 0 or 1; and p is an integer of 1 to 1,000.

A second object of this invention is to provide a method of inhibiting bacterial colonization of a bacteria selected from the group consisting of *S. pneumoniae, H. influenza, H. parainfluenzae, Burkholderia (Pseudomonas) cepacia* and a mixture thereof in a patient diagnosed with pneumonia.

Another object of this invention is to provide a method of inhibiting colonization of a bacteria selected from the group consisting of *S. pneumoniae, H. influenza, H. parainfluenzae, Burkholderia (Pseudomonas) cepacia* and a mixture thereof in a patient diagnosed with bacterial bronchitis.

Another object of the invention is to provide a method of inhibiting bacterial colonization of a bacteria selected from the group consisting of *S. pneumoniae, H. influenza, H. parainfluenzae, Burkholderia (Pseudomonas) cepacia* and a mixture thereof in a patient diagnosed with otitis media.

Another object of this invention is to provide a novel pharmaceutical composition containing a compound of Formula I,

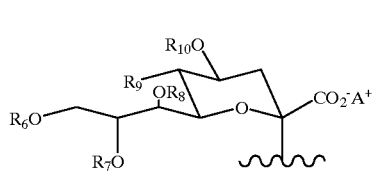

where

R$_1$ is H, (β-1)GalNAc-, SO$_3$B (where B is H or a cation) or a sialic acid of Formula II;

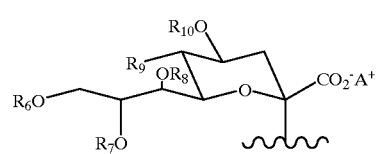

where

R$_6$, R$_7$, R$_8$, and R$_{10}$ are each independently H, C$_{1-6}$ acyl, lactyl, C$_{1-6}$ alkyl, sulfate, phosphate, anhydro, a sialic acid of Formula II, (α-1)Fuc, (β-1)Glc or (β-1)Gal;

R$_9$ is NH-C$_{1-6}$ acyl, glycolylamido, amino or hydroxyl; and

A is H or a cation;

R$_2$ is H or (α-1)Fuc-;

R$_3$ and R$_4$ are each independently OH or NHAc;

R$_5$ is H, SO$_3$B (where B is H or a cation) or a sialic acid of Formula II as defined above; and Y is a chemical bond or a linking group;

Z is H or a multivalent support;

m is 0 or 1; and p is an integer of 1 to 1,000 wherein when R$_5$ is H, R$_1$ is not H and when R$_1$ is a sialic acid, R$_2$ is not (α-)Fuc.

In a preferred embodiment, the compound of Formula I is of the formula

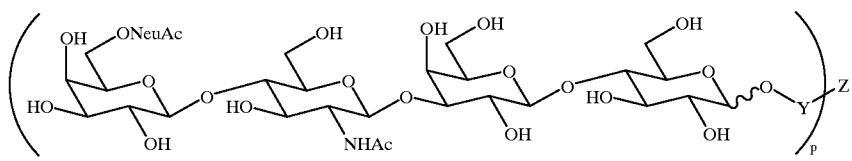

where

Y is a chemical bond or a linking group;

Z is H or a multivalent support; and p is an integer of 1 to 1,000.

These and other objects of the present invention are enabled by the inventors' discovery that a bacteria selected from the group consisting of S. pneumoniae, H. influenza, H. parainfluenzae, Burkholderia (Pseudomonas) cepacia and a mixture thereof can be inhibited from colonizing, by a compound of Formula I.

DETAILED DESCRIPTION OF THE PREFERRED EMBODIMENTS

The following abbreviations are used throughout the text: "Gal" for galactose; "Glc" to glucose, "GlcNac" for N-acetylglucosamine; "GalNAc" for N-acetylgalactosamine; "Fuc" for fucose; "NAN or NeuAc" for N-acetylneuraminic acid.

Specific oligosaccharide compounds may include NeuAcα2-6-Galβ1-4-GlcNAcβ1-3-Galβ1-4-Glc, NeuAcα2-3-Galβ1-4-GlcNAcβ1-3-Galβ1-4-Glc, Galβ1-4-GlcNAcβ1-3-Galβ1-4-Glc, NeuAcα2-6-Galβ1-4-[Fucα1-3]GlcNAcβ1-3-Galβ1-4-Glc, NeuAcα2-6-[GalNAcβ1-3] Galβ1-4-GlcNAcβ1-3-Galβ1-4-Glc, NeuAcα2-6-[GalNAcβ1-3]Galβ1-4-[Fucα1-3]GlcNAcβ1-3-Galβ1-4-Glc, NeuAcα2-6-Galβ1-4-GlcNAc, NeuAcα2-6-Galβ1-4-[Fucα1-3]GlcNAc, NeuAcα2-6-[GalNAcβ1-3]Galβ1-4-GlcNAc, NeuAcα2-6-[GalNAcβ1-3]Galβ1-4-[Fucα1-3]GlcNAc, GalNAcβ1-3-Galβ1-4-GlcNAcβ1-3-Galβ1-4-Glc, GalNAcβ1-3-Galβ1-4-GlcNAc, GalNAcβ1-3-Galβ1-4-Glc, NeuAcα2-3-Galβ1-4-GlcNAc, NeuAcα2-6-Galβ1-4-GlcNAcβ1-3-Galβ1-4-GlcNAc, NeuAcα2-3-Galβ1-4-GlcNAcβ1-3-Galβ1-4-GlcNAc, Galβ1-4-GlcNAcβ1-3-Galβ1-4-GlcNAc, NeuAcα2-6-Galβ1-4-[Fucα1-3]GlcNAcβ1-3-Galβ1-4-GlcNAc, NeuAcα2-6-[GalNAcβ1-3]Galβ1-4-GlcNAcβ1-3-Galβ1-4-GlcNAc, NeuAcα2-6-[GalNAcβ1-3]Galβ1-4-[Fucα1-3]GlcNAcβ1-3-Galβ1-4-GlcNAc, GalNAcβ1-3-Galβ1-4-GlcNAcβ1-3-Galβ1-4-GlcNAc and GalNAcβ1-3-Galβ1-4-GlcNAc.

A preferred group of oligosaccharide compounds are the above-identified group, excluding the compound Galβ1-4-GlcNAcβ1-3-Galβ1-4-Glc.

Each of these compounds also can be administered in monovalent (i.e. p=1) or in multivalent form (i.e. p=2–1, 000), either with or without a linker group Y. In addition, the linking group Y can be bonded directly to Z where Z is H, or a multivalent support.

The oligosaccharides of the present invention may be obtained using any known method, including (1) enzymatically, using one of the method described in U.S. Pat. No. 5,180,674, (2) synthetically, using classical organic chemistry, (3) by degradation of a natural occurring oligosaccharide, glycolipid, or glycopeptide or (4) isolation from natural source such as human milk. The isolation of LSTc is reported by Kuhn. R. and Gauche. A, Chem Ber., 95, 513 (1962) and Dorland et al. Eur. J. Bioch. 87, 323 (1978)

For example the compound NeuAcα2-6-Galβ1-4-GlcNAcβ1-3-Galβ1-4-Glc, can be prepared enzymatically from lactose. Accordingly lactose is reacted with a β galactoside β1-3 N-acetylglucosaminlytransferase and UDP-GlcNAc, a βN-acetylglucosaminoside β1-4 galactosyltransferase and UDP-Gal and a β galactoside α2-3 sialyltransferase and CMP-NeuAc under suitable conditions to affect transfer of the three sugar groups from the sugar nucleotides to the appropriate acceptor molecule.

The groups $R_1$ and $R_5$ can be a group $SO_3B$, where B can be either H or a cation. Accordingly, the compound of Formula I includes sulfate substitute and salts thereof. Suitable cations include alkali metals, alkaline earth metals or ammonium. Any known suitable pharmaceutically acceptable cations may be used, including the cations of conventional non-toxic salts including a metal salt such as an alkali metal salt (e.g. sodium salt, potassium salt, etc.) or an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N, N'-dibenzylethylenediamine salt, etc.), an organic acid salt (e.g. formate, acetate, trifluoroacetate, maleate, tartrate, methanesulfonate, benzenesulfonate, toluenesulfonate, etc.), an inorganic acid salt (e.g. hydrochloride, hydrobromide, sulfate, phosphate, etc.), a salt with an amino acid (e.g. arginine salt, aspartic acid salt, glutamic acid salt, etc.), and the like.

The compound of Formula I can also be the corresponding aza sugar, in which the oxygen of one or more of the pyran rings is replaced with a nitrogen, to form a piperidine ring system.

The aza sugars corresponding to Formula I can be prepared by conventional methods known to those of ordinary skill in the art such as through classical organic chemistry techniques or enzymatically using the appropriate aza saccharide as the acceptor substrate. Aza sugar nucleotides can be transferred by the corresponding glycosyltransferase for the natural sugar. Aza glucose can be isolated from natural sources and can be converted to the aza lactose by the action of a galactosyltransferase in the presence of a galactose donor such as UDP-gal.

The compound of Formula I can also be the corresponding thio sugar, in which the oxygen of one or more of the pyran rings is replaced with a sulfur, to form a tetrahydrothiopyran ring system.

The thio sugars corresponding to Formula I can be prepared by conventional methods known to those of ordinary skill in the art such as through classical organic chemistry techniques or enzymatically using the appropriate thio saccharide as the acceptor substrate. A monothiosaccharide can be prepared by conventional classical organic chemical techniques from the corresponding monosaccharide.

The compound of Formula II is a sialic acid, which is a family of 9-carbon carboxylated sugars related to neuraminic acid. The carboxylic acid may be in the form of a free acid, when A is H or a salt, when A is a cation.

Suitable cations include alkali metals, alkaline earth metals or ammonium. Any known suitable pharmaceutically acceptable cations may be used, including the cations of conventional non-toxic salts including a metal salt such as an alkali metal salt (e.g. sodium salt, potassium salt, etc.) or an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N, N'-dibenzylethylenediamine salt, etc.), an organic acid salt (e.g. formate, acetate, trifluoroacetate, maleate, tartrate, methanesulfonate, benzenesulfonate, toluenesulfonate, etc.), an inorganic acid salt (e.g. hydrochloride, hydrobromide, sulfate, phosphate, etc.), a salt with an amino acid (e.g. arginine salt, aspartic acid salt, glutamic acid salt, etc.), and the like.

Preferably the compound of Formula II is selected from the group consisting of N-acetyl-neuraminic acid, N-glycolyl-neuraminic acid, keto-deoxy-nonulosonic acid, 9-O-acetyl N-acetyl-neuraminic acid, 9-O-acetyl N-glycolyl-neuraminic acid, 9-O-acetyl-keto-deoxy-nonulosonic, 7-O-acetyl-N-acetyl-neuraminic acid, 7-O-acetyl-N-glycolyl-neuraminic acid, 4-O-acetyl-N-acetyl-neuraminic acid, 4-O-acetyl-N-glycolyl-neuraminic acid, 7,9-di-O-acetyl-N-acetyl-neuraminic acid, 8,9-di-O-acetyl-N-acetyl-neuraminic acid, 7,9-di-O-acetyl-N-glycolyl-neuraminic acid, 8,9-di-O-acetyl-N-glycolyl-neuraminic acid, 4,9-di-O-acetyl-N-acetyl-neuraminic acid, 7,8,9-tri-O-acetyl-N-acetyl-neuraminic acid, 7,8,9-tri-O-acetyl-N-glycolyl-neuraminic acid, 9-O-lactyl-N-acetyl-neuraminic acid, 9-O-lactyl-N-glycolyl-neuraminic acid, 4-O-acetyl-9-O-lactyl-N-acetyl-neuraminic acid, 4-O-acetyl-9-O-lactyl N-glycolyl-neuraminic acid, 8-O-methyl-N-acetyl-neuraminic acid, 8-O-methyl-N-glycolyl-neuraminic acid, 8-O-methyl-9-O-acetyl-N-glycolyl-neuraminic acid, 8-O-methyl- 7,9-di-O-acetyl-N-glycolyl-neuraminic acid, 8-O-sulpho-N-glycolyl-neuraminic acid, 8-O-phosphoro-N-acetyl-neuraminic acid, 2,3 didehydro 2,6 anhydro-N-acetyl-neuraminic acid, 9-O-acetyl-2,3 didehydro 2,6 anhydro-N-acetyl-neuraminic acid, 9-O-lactyl-2,3 didehydro 2,6 anhydro-N-acetyl-neuraminic acid, 2,3 didehydro 2,6 anhydro-N-glycolyl-neuraminic acid, 9-O-acetyl-2,3 didehydro 2,6 anhydro-N-glycolyl-neuraminic acid, 9-O-lactyl-2,3 didehydro 2,6 anhydro-N-glycolyl-neuraminic acid, 8-O-methyl-2,3 didehydro 2,6 anhydro-N-glycolyl-neuraminic acid, 2,7 anhydro-N-acetyl-neuraminic acid, 2,7 anhydro-N-glycolyl-neuraminic acid, 8-O-methyl-2,7 anhydro-N-glycolyl-neuraminic acid, 4,8 anhydro-N-acetyl-neuraminic acid and salts thereof. More preferably the sialic acid of Formula II is N-acetyl-neuraminic acid or N-glycolyl-neuraminic acid. These sialic acids are described in A. Varki *Glycobiology* v2, (1992) p25–40. Accordingly the reference describes sources of the sialic acids as well as the appropriate sialyltransferase necessary for enzymatic synthesis of oligosaccharides of Formula I.

When the compound of Formula II is substituted with a sialic acid, the substitution is preferably at the $R_7$ position.

The linking group Y is any group which serves to link the oligosaccharide portion of the compound of Formula I, with the group Z. Suitable linking groups include saccharides, oligosaccharides, peptides, proteins, $C_{2-20}$ alkyl, oxyalkylene chains or any other group, which does not diminish the binding inhibiting activity of the oligosaccharide portion of the compound of Formula I. In addition, the linking group can be a chemical bond, in which case the oligosaccharide portion of the compound of Formula I is directly bound to the group Z.

The oligosaccharide can be provided as a multivalent molecule according to Formula I (i.e. p=2–1,000). In this embodiment the oligosaccharide portion is bound to a multivalent support using known techniques so as to produce a conjugate in which more than one individual molecule of the oligosaccharide is covalently attached, through the group Y to the multivalent support. The multivalent support is sufficiently long to provide a multivalent molecule leaving from between 2–1,000 (i.e. p=an integer of 2–1,000), preferably 2–100, more preferably 2–50 molecules of the oligosaccharide portion bound to the multivalent support.

A suitable multivalent support is a compound with multiple binding sites, to a terminal end of the linking group which is not bound to the reducing end saccharide, or with multiple binding sites to the $C_1$ glycosidic oxygen of a glucose or N-acetylglucosamine residue. Examples include but are not limited to a polyol, a polysaccharide, polylysine, avidin, a polyacrylamide, dextran, lipids, lipid emulsions, liposomes, a dendrimer, human serum albumin, bovine serum albumin or a cyclodextrin.

The chemistry necessary to link the reducing end saccharide (i.e., Glc or GlcNAc) with the linking group Y and to link the linking group Y to the multivalent support is well known in the field of linking chemistry. For example a bond between the reducing end saccharide and Y can be formed by reacting an aldehyde or carboxylic acid at $C_1$ of the reducing end saccharide or any aldehyde or carboxylic acid group introduced onto the reducing end saccharide by oxidation, with the Y group, to form a suitable bond such as —NH—, —N(R')— where R' is $C_{1-20}$ alkyl, a hydroxyalkylamine, a amide, an ester, a thioester, a thioamide.

The bond between the reducing end saccharide and Y can be formed by reacting the $C_1$ hydroxyl group, in the pyranose form, with an acylating agent and a molecular halide, followed by reaction with a nucleophile to form a suitable bond such as —NH—, —N(R')— where R' is $C_{1-20}$ alkyl, —S— and —O—. This type of linking chemistry is described by Stowell et al *Advances in Carbohydrate Chemistry and Biochemistry*, 37 (1980) p 225+.

The oligosaccharide portion can be bound directly (i.e. Y is a chemical bond) to the multivalent support via the free anomeric carbon of the reducing end saccharide. Alternatively, the reducing end saccharide can be bound via a phenethylamine-isothiocyanate derivative as described by Smith et al. *Complex Carbohydrates part C, Methods in Enzymology*, volume L, Ed by V. Ginsburg (1978), p 169–171. It is preferable that the oligosaccharide of Formula I remain soluble in water. It is also possible however to administer the oligosaccharide of Formula I in the form of a suspension in a suitable carrier.

The method of inhibiting bacterial colonization is achieved by administering a binding inhibiting effective amount of the oligosaccharide of Formula I, to a patient in need thereof. The method of administration will be dependant on the desired site of delivery of the oligosaccharide. For example to treat respiratory infections, the oligosaccharide is administered to the nasopharynx, lung or bronchi, preferably in the form of an aerosol. To treat otitis media, the oligosaccharide is administered to the nasopharynx, preferably in the form of drops. To treat conjunctivitis, the oligosaccharide can be administered to the conjunctive tissue, preferably in the form as eye drops or an eye ointment.

Suitable compositions may take the form of a solution, suspension or any pharmaceutically acceptable form suitable for delivery to the site of infection, especially the lungs, bronchial passage, nasopharynx or middle ear. The oligosaccharide can also be administered to the lungs and bronchial passage in the form of an aerosolized dry powder.

The pharmaceutical compositions are usually administered as a mixture with a carrier suitably selected depending upon the route for administration using standard formulations.

A solution or suspension may be prepared by adding any diluent customarily, used in the art. For example, suitable diluents include water (bacteriostatic, sterile and/or pyrogen free), ethyl alcohol, propylene glycol, polyoxyethylene sorbitol, and sorbitan esters. Sodium chloride, glucose or glycerol may be incorporated into such a liquid preparation in an amount sufficient to prepare an isotonic solution.

The oligosaccharides of Formula I may also be administered in conjunction with an antibiotic with activity against a bacteria selected from the group consisting of *S.*

*pneumoniae, H. influenza, H. parainfluenzae, Burkholderia* (*Pseudomonas*) *cepacia* and a mixture thereof. Examples of suitable classes of antibiotics include aminoglycosides, amphenicols, ansamycins, β-lactams such as carbapenems, cephalosporins, cephamycins, monobactams, oxaceaphems and penicillins, lincosamides, macrolides, polypeptides, tetracyclines, 2,4-diaminopyrimidines, nitrofurans, quinolones, sulfonamides, sulfones, β-lactamase inhibitors and antifungal antibiotics such as polyenes. Specific examples of suitable antibiotic compounds include, but are not limited to metronidazole, tetracycline, bismuth, erythromycin, sulfonamide, penicillin, cephalosporin, amoxicilin, cycloserine, fosfomycin, vancaomycin, bacitracin, polymyxins, mitomycin, novobiocin, actinomycin, rifampicin, clindamycin, lincomycin, isoniazid, flucytosine, chloramphenicol, puromycin, fusidic acid, griseofulvin, p-aminosalicylic acid, trimaethoprim, imipenem. Suitable antibiotics also include antibiotic compounds as identified in the *Merck Index, Eleventh edition*, especially those listed on pages THER-9, THER-10 and THER-13, the entire contents of which are hereby incorporated by reference. The amount of antibiotic administered in conjunction with the present oligosaccharide is about the same amount administered for its known therapy. Accordingly, effective dosage of the antibiotic can be determined by routine experimentation.

The therapeutic composition may also further contain ordinary dissolving aids, buffers, pain-alleviating agents, art preservatives, and optionally coloring agents, fragrances, flavors, sweeteners and other pharmacologically active agents such as are well known in the art.

The pharmaceutical compositions are preferably formulated to provide an isotonic solution. The pH of such compositions is preferably at a pH of from 6 to 8, preferably from 6.8 to 7.7, more preferably at physiological pH.

Typically, suitable patients are humans. However the present method is also applicable to treatment of animals, including but not limited to mammals such as pigs, cows, horses, sheep, goats, dogs, cats, rodents and non-human primates.

According to a preferred embodiment of the present invention, the oligosaccharide containing pharmaceutical composition is administered as an aerosol to a patient in need thereof to inhibit binding or eliminate colonies of a bacteria selected from the group consisting of *S. pneumoniae, H. influenza, H. parainfluenzae, Burkholderia* (*Pseudomonas*) *cepacia* and a mixture thereof from the patient's throat, conjunctiva, lungs or bronchial passage.

For aerosol administration, the oligosaccharide compound of Formula I, is preferably supplied in finely divided form along with a surfactant and propellant. Typical amounts of the oligosaccharide of Formula I are about 0.5 to 30 wt. %, preferably about 1 to 10 wt. %. The surfactant is nontoxic and preferably is soluble in the propellant. Representative of such surfactant agents are the esters or partial esters of fatty acids containing from 6 to 22 carbon atoms, such as caproic, octanoic, lauric, palmitic, stearic, linoleic, linolenic, olesteric, and oleic acids, with an aliphatic polyhydric alcohol or its cyclic anhydride such as, for example, ethylene glycol, glycerol, erythritol, ariabitol, mannitol, sorbitol, the hexitol anhydrides derived from sorbitol, and the polyoxyethylene and polyoxypropylene derivatives of these esters. Mixed esters, such as mixed or natural glycerides can be employed. The surfactant can constitute about 0.1 to about 20 percent by weight of the composition, and preferably about 0.25 to about 5 percent.

The balance of the composition is ordinarily propellant. Liquified propellants are typically gases at ambient conditions, and are condensed under pressure. Among suitable liquified propellants are the lower alkanes containing up to 5 carbons, such as butane and propane; and preferably fluorinated or a fluorochlorinated alkane such as R-11. Mixtures of the above can also be employed. In producing the aerosol, a container equipped with a suitable valve is filled with the appropriate propellant, containing the finely divided compounds and surfactant. The ingredients are thus maintained at an elevated pressure until released by action of the valve.

For administration as an aerosol, generation of such an aerosol is accomplished by conventional means, known to those of ordinary skill in the art of drug delivery.

When administered as an aerosol in monovalent form, for the treatment of a respiratory infection, the composition is formulated to provide a concentration in the mucus membranes of from 0.0001 to 20 mg/mL, preferably 0.01 to 10 mg/mL.

When administered as a multivalent molecule for the treatment of a respiratory infection, an aerosol pharmaceutical composition comprising the oligosaccharide of Formula I is administered so as to achieve a concentration in the mucus membranes of 0.00001 to 2 mg/mL, preferably 0.001 to 1 mg/mL.

According to another embodiment of the present invention, the oligosaccharide containing pharmaceutical composition is administered via the nasopharynx to the ear of a patient in need thereof to inhibit binding, or eliminate colonies of bacteria selected from the group consisting of *S. pneumoniae, H. influenza, H. parainfluenzae, Burkholderia* (*Pseudomonas*) *cepacia* and a mixture thereof from a patient's middle ear. A patient in need thereof is typically diagnosed with otitis media.

The mode of administration is such as to deliver a binding inhibiting effective amount of the oligosaccharide of Formula I, to the site of infection. This can typically be achieved by administering nasal drops or spray containing the oligosaccharide of Formula I, via the nasopharynx, to the ear. The oligosaccharide of Formula I can also be administered in the form of an oral mouthwash, in which the oligosaccharide is delivered to the site of infection by the action of gargle and reflux.

When administered to the ear, a suitable form is a liquid solution or suspension in a non-toxic pharmaceutically acceptable diluent or solvent, for example, as a solution in 1,3-butanediol. Among the acceptable vehicles and solvents that may be employed are water, Ringer's solution and isotonic sodium chloride solution. In addition, sterile fixed oils are conventionally employed as a solvent or suspending medium. For this purpose, any bland fixed oil may be employed including synthetic mono- or di-glycerides. In addition, fatty acids such as oleic may find use in the preparation of injectables.

When administered to the ear in monovalent form, for the treatment of otitis media, the composition is formulated to provide a concentration at the site of infection of from 0.0001 to 20 mg/mL, preferably 0.01 to 10 mg/mL.

When administered as a multivalent molecule for the treatment of otitis media, the composition is formulated to provide a concentration at the site of infection of 0.00001 to 2 mg/mL, preferably 0.001 to 1 mg/mL.

According to another embodiment of the present invention, the oligosaccharide containing pharmaceutical composition is administered to the eye to a patient in need thereof to inhibit binding or eliminate colonies of a bacteria selected from the group consisting of *S. pneumoniae, H. influenza, H. parainfluenzae, Burkholderia (Pseudomonas) cepacia* and a mixture thereof from a patient's eye. A patient in need thereof is typically diagnosed with conjunctivitis.

When administered to the eye, a suitable form is a liquid solution or suspension in a non-toxic pharmaceutically acceptable diluent or solvent, for example, as an ophthalmic saline solution.

When administered to the eye in monovalent form, for the treatment of conjunctivitis, the composition is formulated to provide a concentration at the site of infection of from 0.0001 to 20 mg/mL, preferably 0.01 to 10 mg/mL.

When administered as a multivalent molecule for the treatment of conjunctivitis, the composition is formulated to provide a concentration at the site of infection of 0.00001 to 2 mg/mL, preferably 0.001 to 1 mg/mL.

These dosages can be achieved by administration, at least daily, preferably twice daily, more preferably three times a day and most preferably four times a day.

The present invention can also be used to prevent a bacterial infection of *S. pneumoniae, H. influenza, H. parainfluenzae* and *Burkholderia (Pseudomonas) cepacia*, in a patient in need thereof. While it is generally desirable to prevent a bacterial infection in all patients who are asymptomatic for a bacterial infection, there is an identifiable population, for which the consequences of a bacterial infection make the risk of a bacterial infection unacceptable. Specifically, the consequences of a bacterial infection in the young, old or immunocompromised are especially devastating. Accordingly, the oligosaccharide of Formula I can be administered to a patient in need of prevention of a bacterial infection of *S. pneumoniae, H. influenza, H. parainfluenzaea*nd *Burkholderia (Pseudomonas) cepacia* in an amount sufficient to prevent bacterial infection.

For the prevention of a respiratory bacterial infection, the oligosaccharide of Formula I is typically administered in monovalent form to provide a concentration in the mucus membranes of from 0.0001 to 20 mg/mL, preferably 0.01 to 10 mg/mL. These prophylactic dosages can be achieved by administration, at least daily, preferably twice daily.

When administered as a multivalent molecule for the prevention of a respiratory infection, an aerosol pharmaceutical composition comprising the oligosaccharide of Formula I is administered so as to achieve a concentration in the mucus membranes of 0.00001 to 2 mg/mL, preferably 0.001 to 1 mg/ML.

When administered via the nasopharynx to the ear for the prevention of otitis media, the composition is formulated in a monovalent form to provide a concentration in the membranes of the ear of from 0.0001 to 20 mg/mL, preferably 0.01 to 10 mg/mL.

When administered via the nasopharynx as a multivalent molecule to the ear for the prevention of otitis media, for treating otitis media comprising the oligosaccharide of Formula I is administered so as to achieve a concentration at the membranes of the ear of 0.00001 to 2 mg/mL, preferably 0.001 to 1 mg/mL.

The composition of the pharmaceutical composition of the invention, is basically as described above for the inhibition of bacterial infections. The amount of the oligosaccharide of Formula I will vary depending on the mode of administration, based on the amount necessary to deliver a binding inhibiting effective amount to the site of the infection. Generally the pharmaceutical will contain the oligosaccharide at a concentration of about 0.01 to 2,000 mg/mL, preferably 1 to 1,000 mg/mL in monovalent form, and from 0.001 to 200 mg/mL, preferably from 0.1 to 100 mg/mL in multivalent form.

Other features of the invention will become apparent in the course of the following descriptions of exemplary embodiments which are given for illustration of the invention and are not intended to be limiting thereof.

Throughout the examples section the following abbreviations are used:

LSTc: NeuAcα2-6-Galβ1-4-GlcNAcβ1-3-Galβ1-4-Glc

LNnT: Galβ1-4-GlcNAcβ1-3-Galβ1-4-Glc

LSTd (3'LSTc): NeuAcα2-3-Galβ1-4-GlcNAcβ1-3-Galβ1-4-Glc

GalNAc β1-3 LNnT: GalNAcβ1-3-Galβ1-4-GlcNAcβ1-3-Galβ1-4-Glc

HSA: human serum albumin

EXAMPLE 1

Synthesis of NeuAcα2-6-Galβ1-4-GlcNAcβ1-3-Galβ1-4-Glc

Lactose was contacted with UDP-N-acetylglucosamine and a β-galactoside β1-3 N-acetylglucosaminyl transferase purified from pig serum in a 0.1 M HEPS buffered aqueous solution at 37° C. The product trisaccharide was then contacted with UDP-Gal and a β-N-acetylglucosaminoside β1-4 Galactosyltransferase isolated from bovine milk, in a 0.1 M HEPS buffered aqueous solution at 37° C. The product tetrasaccharide was then contacted with CMP-NAN and a β-galactoside α2-6 sialyltransferase isolated from rat liver in a 0.1 M HEPES buffered aqueous solution at 37° C. The title pentasaccharide was isolated by conventional methods.

EXAMPLE 2

A method similar to that of Rostand. K. and Esko. (1993) J. Biol. Chem. 268 pp 24053–3, which studied the binding of radiolabelled *P. aeruginosa* to CHO cells was used to test for the binding inhibition of oligosaccharide compounds. For the studies described herein, *S. pneumoniae* (strains R-6, P70, and other clinical respiratory isolates) were labelled by culture in lysine-deficient tryptic soy broth containing $^3$H-lysine. The tryptic soy broth was made deficient in lysine by pretreating it with lysine decarboxylase from *E.coli*. The bacteria were cultured for 4–5 hours, at which point the culture was in exponential growth. The bacteria were harvested and washed in Leibovitz L-15 Medium supplemented with 0.2% low-endotoxin bovine serum albumin. The bacteria were diluted to approximately $3 \times 10^8$/mL, and then mixed 1:1 with either L-15-BSA or with various compounds to be tested. The bacterial mixtures were incubated at room temperature, with gentle agitation on an orbital shaker. After 10–15 min, samples of the bacterial mixtures were transferred to the surface of a confluent monolayer of cultured epithelial cells in a 96-well polystyrene plate. The cells most commonly used were the Wong-Kilbourne derivative of Chang conjunctiva. The human nasopharyngeal cell line Detroit 562, and the human lung cell line A549 were also used. The bacteria were incubated with the cells for 30 min with gentle agitation, at room temperature. The unbound bacteria were washed away with PBS containing 0.2% bovine serum albumin. Scintillant solution was added to the wells, and the plate was put in a microplate scintillation counter for quantitation of bound bacteria.

Adhesion of *H. influenzae* to epithelial cells was performed with the same protocol with the following modifications: The bacteria were cultured overnight in lysine-deficient Haemophilus test media. The bacteria were incubated with the cells at a concentration near $10^7$/mL for 60 min.

Inhibition of adherence of *S. pneumoniae* to respiratory epithelial cells

| Bacteria | IC$_{50}$ (mM) | | | | | | |
|---|---|---|---|---|---|---|---|
| | Det-562 | FaDu | CaLu-3 | 1° lung | A549 | HU-VEC | CHANG |
| LSTc | | | | | | | |
| *S. pneumoniae* | 5.4 | 4.0 | 4.4 | 0.4 | 0.1 | 0.1 | 1.5 |
| *P. cepacia* | | | 1 | | | | |
| LSTc-HSA[3] | | | | | | | |
| *S. pneumoniae* | 0.10 | | 0.0004 | | | | |
| *H. influenzae* | 0.03 | | | | | | |

Det-562 and FaDu: nasopharyngeal carcinomas
CaLu-3 and A459[1]: lung carcinomas
1° lung: rat tracheal primary epithelium
HUVEC[2]: human umbilical vein endothelial cells
[1]cells activated with IL1α
[2]cells activated with TNFα or thrombin.
[3]LSTc bound to a human serum albumin backbone; the molar ratio of oliaosaccharide:prot = 20:1. Oligosaccharide molarity is given.

EXAMPLE 3

In vivo experiments with LSTC and LNnT.

Rabbits. *S. pneumoniae* strain AII were mixed with oligosacchardies and administered to New Zealand white rabbits by tracheal instillation, and lung lavage colonies were counted at the indicated time by the method described in Saukkonen, et al., 1991, J. Exp. Med. 173:1143–9.

Colonization of rabbit lungs with *S. pneumoniae* in the presence of an adherence-inhibitory oligosaccharide

| | | CFU* | | |
|---|---|---|---|---|
| | Conditions | LSTc (100 μM) | LNnT (100 μM) | Control (saline) |
| 1 | Inoculum: 5 × 10⁵ bacteria; intratracheal; 24 h lavage | 1.4 × 10⁵, 9.1 × 10³ | 8.7 × 10², 4.7 × 10³ | 7.5 × 10⁴, 7.1 × 10⁵ |
| | 4 day lavage | <10, <10 | <10, <10 | 1.6 × 10⁴, 4.5 × 10³ |
| 2 | Inoculum: 5 × 10⁵ bacteria intratracheal 4 day lavage | 0, 0 | 0, 0 | 1.6 × 10⁴, 4.5 × 10³ |
| 3 | Inoculum: 5 × 10⁷ bacteria**; intracheal; 24 h lavage | 0, 0 | 0, 0 | 3.1 × 10⁵, 2.2 × 10⁴ |
| 4 | inoculum: 10⁵ | | 1.1 × 10³, | 1.4 × 10⁵, |

| | IC$_{50}$ (mM) [mean (SD)] | | | | | | |
|---|---|---|---|---|---|---|---|
| | CELL LINE[1] | | | | | | |
| | Det-562 | FaDu | CaLu-3 | 1°lung | A549[2] | HUVEC[3] | Chang |
| Monovalent | | | | | | | |
| LNnT | 7.0 | | >16.0 | | 0.095 (0.005) | 0.052 (0.022) | 8.0 |
| LSTc | 4.0 | 4.5 | 4.4 | 0.25 | 0.069 (0.032) | 0.069 (0.035) | 1.4 |
| LSTd (3'LSTc) | | | | | 0.095 (0.005) | 0.090 | 0.6 |
| GalNAc β1-3 LNnT | | | | | 0.080 | 0.075 | |
| GalNAc β1-3 Galβ1-4 Glc | | | | | 0.085 | 0.070 | >6.0 |
| Multivalent[4] | | | | | | | |
| LNnT | >0.500 | | | | 0.100 | 0.030 (0.020) | |
| LSTc | 0.125 | 0.160 | 0.110 | 0.250 | 0.021 (0.006) | 0.023 (0.012) | |
| GalNAc β1-3 Gal-HSA | 0.500 | 0.020 | 0.100 | 0.0004 | 0.100 | 0.087 (0.018) | |

[1]Detroit-562 and FaDu: human nasopharyngeal carcinoma
CaLu-3 and A549: human lung carcinoma
HUVEC: human umbilical vein endothelial cells (primary)
Rat trachea epithelial monolayer (primary)
Chang: human conjunctival carcinoma
[2]Activated with IL1α
[3]Activated with TNFα or thrombin
[4]Human serum albumin backbone; molar ratio of oligosaccharide:prot = 20:1. Oligosaccharide molar concentrations are given.

-continued

| Conditions | LSTc (100 μM) | LNnT (100 μM) | Control (saline) |
|---|---|---|---|
| bacteria; intratracheal; 24 h lavage | | $1.4 \times 10^3$ | $1.4 \times 10^5$ |

*Lungs were lavaged on day 4 and fluid was quantitatively plated on blood agar for counting of bacterial colonies/ml lavage fluid. 2 rabbits/group.
**Saline control animals given this high inoculum became very sick, with lungs heavily colonized. One rabbit was bacteremic ($10^4$ CFU/ml blood). Oligosaccharide treated animals were healthy throughout the experiment.

EXAMPLE 4

Treatment of rabbits Pre-colonized with *S. pneumoniae* with adherence-reversing oligosaccharide.

*S. pneumonaie* strain AII were administered to New Zealand white rabbits by tracheal instillation. All rabbits were sick at 24h, with indications of pneumonia. After 24h oligosaccharide (LNnT) or control (saline) was administered intratracheally. After an additional 24 h lung lavage colonies were counted as described in Example 3.

| | CFU | |
|---|---|---|
| Conditions | LNnT (100 μM) | Control (Saline) |
| Inoculum: $10^5$ bacteria intratracheal lavage 24 h after oligosaccharide treatment and 48 h after bacterial instillation | 0,0 | $5.4 \times 10^3$, $4.8 \times 10^3$ |

At 48h the LNnT-treated rabbits were healthy, whereas saline control rabbits were ill, with bloody, congested lungs.

EXAMPLE 5

Rats: Newborn Sprague-Dawley rats were inoculated with $10^6$ *S. pneumoniae* strain SIII intranasally in a volume of 20 μl saline. At the indicated time nasal cavity was lavaged and plated over blood agar in serial dilutions for determination of the number of colonies.

Colonization of rat nasopharynx with *S. pneumoniae* in the presence of an adherence-inhibitory oligosaccharide

| | | CFU* | |
|---|---|---|---|
| Conditions | LSTc-HSA (100 μM) | LNnT-HSA (100 μM) | Control (saline) |
| 1 Inoculum: $10^6$ bacteria; intranasal; 4 rats/group; 3 hour nasal lavage | $4.1(\pm 1.0) \times 10^4$ | $3.5(\pm 0.4) \times 10^4$ | $8.8(\pm 0.8) \times 10^4$ |
| 7 day nasal lavage | $3 \pm 1$ | $6 \pm 1$ | $268 \pm 62$ |
| 2 Inoculum: $10^6$ bacteria; intranasal; 8 rats/group 5.5 h lavage | $4.1(\pm 0.8) \times 10^4$ | $3.7(\pm 0.9) \times 10^4$ | $8.3(\pm 0.8) \times 10^4$ |

*Nasal cavity was lavaged at the indicated times and the number of CFU/ml lavage fluid was determined.

EXAMPLE 6

Using the testing protocol described in Example 2, four strains of bacteria were tested for binding inhibition by different oligosaccharide compounds.

Inhibition of adherence of other pathogenic bacteria to respiratory epithelial cells

| | $IC_{50}$ (mM) [mean (SD)] | | | |
|---|---|---|---|---|
| Bacteria | *H. influenzae* (strain 46519) | *H. influenzae* (strain 39689) | *H. para-influenzae* (strain 44241) | *Burkholderia* (*Pseudomonas*) *cepacia* |
| CELLS | Chang | Chang | DET-562 | Calu 3 |
| LNnT | >14.0 | >14.0 | | 1 |
| LSTc | | >10.0 | | 5.6 |
| GalNAc β1-3 LNnT | 7.8 (2.9) | >10.0 | | |
| GalNAc β1-3 Gal β1-4 Glc | 4.2 (5.3) | 10.6 (7.7) | | |
| LNnT-HSA | >0.2 | >0.2 | 0.10 | |
| LSTc-HSA | | >0.2 | 0.03 | |
| GalNAc β1-3 Gal-BSA | | | 0.25 | |

*Highest concentration tested is 10–15 mM monovalent oligosaccharides and 0.2–0.25 mM multivalent oligosaccharides, for which the carbohydrate molar concentration is 5 given.

Example 7

10 mL of an isotonic pharmaceutical composition comprising 500 mg of NeuAcα2-6-Galβ1-4-GlcNAcβ1-3-Galβ1-4-Glc, 100 mL of sterile water, and 10 mL of propylene glycol is administered to a human patient diagnosed with pneumonia, in the form of an aerosol. Treatment is continued three times a day, at eight hour intervals, until the bacterial infection has been eliminated.

EXAMPLE 8

5 drops of a pharmaceutical composition comprising 1,000 mg of NeuAcα2-6-Galβ1-4-GlcNAcβ1-3-Galβ1-4-Glc and 100 mL of 1,3-butanediol is administered to the nasopharynx of a human patient diagnosed with otitis media, in the form of drops or nasal spray. Treatment is continued twice a day, at twelve hour intervals, until the bacterial infection has been eliminated.

EXAMPLE 9

5 drops of an ophthalmic solution comprising 800 mg of NeuAcα2-6-Galβ1-4-GlcNAcβ1-3-Galβ1-4-Glc and 100 mL of isotonic saline solution is administered to the eye of a human patient diagnosed with conjunctivitis, in the form of eye drops. Treatment is continued four times a day, at six hour intervals, until the bacterial infection has been eliminated.

EXAMPLE 10

10 mL of an isotonic pharmaceutical composition comprising 500 mg of GalNAcβ-3-Galβ1-4-GlcNAcβ1-3-Galβ1-4-Glc, 100 mL of sterile water, and 10 mL of propylene glycol is administered to a human patient diagnosed with pneumonia, in the form of an aerosol. Treatment is continued three times a day, at eight hour intervals, until the bacterial infection has been eliminated.

EXAMPLE 11

10 mL of an isotonic pharmaceutical composition comprising 500 mg of NeuAcα2-3-Galβ1-4-GlcNAcβ1-3-

Galβ1-4-Glc, 100 mL of sterile water, and 10 mL of propylene glycol is administered to a human patient diagnosed with pneumonia, in the form of an aerosol. Treatment is continued three times a day, at eight hour intervals, until the bacterial infection has been eliminated.

EXAMPLE 12

10 mL of an isotonic pharmaceutical composition comprising 200 mg of NeuAcα2-6-Galβ1-4-GlcNAcβ1-3-Galβ1-4-Glc-HSA, at an oligosaccharide:prot ratio of 20:1, 100 mL of sterile water, and 10 mL of propylene glycol is administered to a human patient diagnosed with pneumonia, in the form of an aerosol. Treatment is continued twice daily, at twelve hour intervals, until the bacterial infection has been eliminated.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent if the United States is:

1. A pharmaceutical composition for inhibiting colonization of bacteria selected from the group consisting of *S. pneumoniae, H. influenzae, H. parainfluenzae, Burkholderia (Pseudomonas) cepacia*, and a mixture thereof, comprising, in association with a carrier or excipient suitable for delivery to the lungs, bronchial passages, nasopharynx or middle ear, a binding inhibiting effective amount of the compound of Formula I, (I)

where $R_1$ is H, (β-1)GalNAc-, $SO_3B$ (where B is H or a cation) or a sialic acid of Formula II;

(II)

where $R_6$, $R_7$, $R_8$, and $R_{10}$ are each independently H, $C_{1-6}$ acyl, lactyl, $C_{1-6}$ alkyl, sulfate, phosphate, anhydro, a sialic acid of Formula II, (α-1)Fuc, (β-1)Glc or (β-1)Gal;

$R_9$ is NH—$C_{1-6}$ acyl, glycolylamido, amino or hydroxyl; and

A is H or a cation;

$R_2$ is H or (α-1)Fuc-;

$R_3$ and $R_4$ are each independently OH or NHAc;

$R_5$ is H, $SO_3B$ (where B is H or a cation) or a sialic acid of Formula II as defined above; and Y is a chemical bond or a linking group;

Z is H or a multivalent support;

m is 0 or 1; and p is an integer of 1 to 1,000 with the proviso that the compound is not Galβ1-4-GlcNAcβ1-3-Galβ1-4-Glc.

2. The composition of claim 1, wherein said compound of Formula I is selected from the group consisting of NeuAcα2-6-Galβ1-4-GlcNAcβ1-3-Galβ1-4-Glc, NeuAcα2-3-Galβ1-4-GlcNAcβ1-3-Galβ1-4-Glc, NeuAcα2-6-Galβ1-4-[Fucα1-3]GlcNAcβ1-3-Galβ1-4-Glc, NeuAcα2-6-[GalNAcβ1-3]Galβ1-4-GlcNAcβ1-3-Galβ1-4-Glc, NeuAcα2-6-[GalNAcβ1-3]Galβ1-4-[Fucα1-3]GlcNAcβ1-3-Galβ1-4-Glc, NeuAcα2-6-Galβ1-4-GlcNAc, NeuAcα2-6-Galβ1-4-[Fucα1-3]GlcNAc, NeuAcα2-6-[GalNAcβ1-3]Galβ1-4-GlcNAc, NeuAcα2-6-[GalNAcβ1-3]Galβ1-4-[Fucα1-3]GlcNAc, GalNAcβ1-3-Galβ1-4-GlcNAcβ1-3-Galβ1-4-Glc, GalNAcβ1-3-Galβ1-4-Glc, NeuAcα2-3-Galβ1-4-GlcNAc, NeuAcα2-6-Galβ1-4-GlcNAcβ1-3-Galβ1-4-GlcNAc, NeuAcα2-3-Galβ1-4-GlcNAcβ1-3-Galβ1-4-GlcNAc, Galβ1-4-GlcNAcβ1-3-Galβ1-4-GlcNAc, NeuAcα2-6-Galβ1-4-[Fucα1-3]GlcNAcβ1-3-Galβ1-4-GlcNAc, NeuAcα2-6-[GalNAcβ1-3]Galβ1-4-GlcNAcβ1-3-Galβ1-4-GlcNAc, NeuAcα2-6-[GalNAcβ1-3]Galβ1-4-[Fucα1-3]GlcNAcβ1-3-Galβ1-4-GlcNAc, GalNAcβ1-3-Galβ1-4-GlcNAcβ1-3-Galβ1-4-GlcNAc, GalNAcβ1-3-Galβ1-4-GlcNAc, and a mixture thereof.

3. The pharmaceutical composition of claim 1, wherein said composition is in a form suitable for administration as an aerosol.

* * * * *